(12) United States Patent
Koizumi et al.

(10) Patent No.: US 11,598,034 B2
(45) Date of Patent: Mar. 7, 2023

(54) STRETCHABLE NON-WOVEN FABRIC HAVING EXCELLENT REPETITION DURABILITY

(71) Applicant: KURARAY CO., LTD., Kurashiki (JP)

(72) Inventors: Satoshi Koizumi, Okayama (JP); Sumito Kiyooka, Okayama (JP); Yasurou Araida, Osaka (JP)

(73) Assignee: KURARAY CO., LTD., Kurashiki (JP)

( * ) Notice: Subject to any disclaimer, the term of this patent is extended or adjusted under 35 U.S.C. 154(b) by 324 days.

(21) Appl. No.: 15/506,423

(22) PCT Filed: Aug. 25, 2015

(86) PCT No.: PCT/JP2015/073874
§ 371 (c)(1),
(2) Date: Feb. 24, 2017

(87) PCT Pub. No.: WO2016/031818
PCT Pub. Date: Mar. 3, 2016

(65) Prior Publication Data
US 2017/0247823 A1 Aug. 31, 2017

(30) Foreign Application Priority Data
Aug. 27, 2014 (JP) .............................. JP2014-172976

(51) Int. Cl.
*D04H 1/50* (2012.01)
*D04H 1/4391* (2012.01)
(Continued)

(52) U.S. Cl.
CPC ........... *D04H 1/50* (2013.01); *A61F 13/0273* (2013.01); *D04H 1/435* (2013.01);
(Continued)

(58) Field of Classification Search
CPC ............................... D04H 1/50; D04H 1/4382
(Continued)

(56) References Cited

U.S. PATENT DOCUMENTS

2004/0116027 A1 6/2004 Termonia et al.
2006/0052022 A1 3/2006 Suzuki et al.
(Continued)

FOREIGN PATENT DOCUMENTS

CN 1714188 A 12/2005
CN 101522972 A 9/2009
(Continued)

OTHER PUBLICATIONS

Machine Translation for JP 2009/097133. (Year: 2009).*
(Continued)

*Primary Examiner* — Peter Y Choi
(74) *Attorney, Agent, or Firm* — Oblon, McClelland, Maier & Neustadt, L.L.P.

(57) ABSTRACT

Provided are a stretchable non-woven fabric including crimped fibers, satisfying the following formula: $(\sigma_{65}-\sigma_{55})/(\sigma_{30}-\sigma_{20})\geq 2.5$, when a stress σ (N/50 mm) at a strain ε of 20%, 30%, 55% and 65% in a stress-strain curve by a tensile test for at least one direction in a plane direction, is referred to as $\sigma_{20}$, $\sigma_{30}$, $\sigma_{55}$ and $\sigma_{65}$, respectively, and a bandage including the non-woven fabric. The non-woven fabric and the bandage lead small deterioration in stretching performance when used repeatedly, and can be excellent in repetition durability.

15 Claims, 4 Drawing Sheets

(51) Int. Cl.
   *D04H 1/4382* (2012.01)
   *A61F 13/02* (2006.01)
   *D04H 1/435* (2012.01)

(52) U.S. Cl.
   CPC ..... *D04H 1/43828* (2020.05); *D04H 1/43832* (2020.05); *D04H 1/43835* (2020.05); *D04H 1/43914* (2020.05); *D04H 1/43918* (2020.05); *D04H 1/4383* (2020.05); *D04H 1/43912* (2020.05); *D10B 2509/02* (2013.01)

(58) Field of Classification Search
   USPC ........................................ 442/328, 329, 361
   See application file for complete search history.

(56) References Cited

U.S. PATENT DOCUMENTS

| | | | | |
|---|---|---|---|---|
| 2008/0261476 | A1* | 10/2008 | Strandqvist | D04H 1/492 442/334 |
| 2010/0035500 | A1 | 2/2010 | Kimura et al. | |

FOREIGN PATENT DOCUMENTS

| | | |
|---|---|---|
| EP | 2 058 424 A1 | 5/2009 |
| JP | 2004-124351 A | 4/2004 |
| JP | 2006-507417 A | 3/2006 |
| JP | 2007-277778 A | 10/2007 |
| JP | 2009-97133 A | 5/2009 |
| JP | 2014-37649 A | 2/2014 |
| JP | 2014-37662 A | 2/2014 |
| KR | 10-2009-0048457 | 5/2009 |
| TW | 200923154 A | 6/2009 |
| WO | 2008/015972 A1 | 2/2008 |
| WO | 2012/070556 A1 | 5/2012 |

OTHER PUBLICATIONS

Translation of Table 1 at paragraph 0112 of JP 2009/097133 to Kimura. (Year: 2009).*
Extended European Search Report dated Jan. 29, 2018 in Patent Application No. 15835543.8, citing document AO therein, 9 pages.
Combined Taiwanese Office Action and Search Report dated Feb. 5, 2018 in Patent Application No. 104128151 (with English translation), citing documents AP and AQ therein, 5 pages.
Combined Chinese Office Action and Search Report dated Jul. 3, 2018 in Chinese Patent Application No. 201580046258.8 (with English translation), citing documents AO, AP and AQ therein, 10 pages.
International Search Report dated Nov. 24, 2015 in PCT/JP2015/073874 filed Aug. 25, 2015.
Information Offer Form issued Oct. 2, 2018 in Japanese Patent Application No. 2016-545548, citing documents AO and AP therein, 39 pages (with English language translation).
Office Action dated Aug. 13, 2020, in Korean patent application No. 10-2017-7006969, with English translation, which cites document AO (8 pages).

* cited by examiner (a)

(b)

STRETCHABLE NON-WOVEN FABRIC HAVING EXCELLENT REPETITION DURABILITY

TECHNICAL FIELD

The present invention relates to a stretchable non-woven fabric that can be suitably used as a bandage or the like.

BACKGROUND ART

A bandage is used not only for directly protecting an application part such as an affected part by being wound around the application part, or for fixing other protecting members (such as gauze) to the application part, but also for stopping bleeding or promoting blood flow to alleviate an edema in a wounded part by a pressurizing force when a bandage is wound with the help of its stretchability. Stretchable bandages are expected for application to a pressure therapy in which treatment is made by pressurizing an affected part, and a typical example of such application is treating or ameliorating a varicose vein of lower extremities.

As a stretchable bandage, a non-woven fabric can be used. By forming a non-woven fabric of crimped fibers that are crimped in coiled forms, and giving an internal structure in which neighboring or crossing crimped fibers are intermingled at crimped coil parts thereof, it is possible to impart stretchability to the non-woven fabric, and it is possible to give a pressurizing force when the non-woven fabric is wound. The non-woven fabric formed of crimped fibers is disclosed, for example, in National Patent Publication No. 2006-507417 (PTD 1), International Publication No. 2008/015972 (PTD 2), and International Publication No. 2012/070556 (PTD 3).

CITATION LIST

Patent Document

PTD 1: National Patent Publication No. 2006-507417
PTD 2: International Publication No. 2008/015972
PTD 3: International Publication No. 2012/070556

SUMMARY OF INVENTION

Technical Problems

For a stretchable bandage, in particular, a stretchable bandage utilizing the pressurizing force at the time of winding for which a relatively long term use is expected (a pressure bandage), repeated usability (for example, even after use for a certain term followed by washing, the bandage is able to give a sufficient pressurizing force and is reusable without any problem) is demanded rather than use in a disposable fashion. Therefore, a non-woven fabric that forms a pressure bandage is desired not to experience deterioration in stretching performance after repeated use, and a conventional stretchable non-woven fabric has a room for improvement in this point.

In light of the above, it is an object of the present invention to provide a stretchable non-woven fabric having little deterioration in stretching performance when used repeatedly and having excellent repetition durability, and a bandage including the same (a pressure bandage and the like).

Solutions to Problems

The present invention provides the following stretchable non-woven fabric and bandage.

[1] A stretchable non-woven fabric including crimped fibers, satisfying $$(\sigma_{65}-\sigma_{55})/(\sigma_{30}-\sigma_{20}) \geq 2.5$$

when a stress σ (N/50 mm) at a strain of 20%, 30%, 55% and 65% in a stress-strain curve by a tensile test for at least one direction in a plane direction, is referred to as $\sigma_{20}$, $\sigma_{30}$, $\sigma_{55}$ and $\sigma_{65}$, respectively.

[2] The non-woven fabric according to [1], wherein a stress $\sigma_{80}$ at a strains of 80% is greater than or equal to 20 N/50 mm.

[3] The non-woven fabric according to [1] or [2], wherein a mass per unit area is greater than or equal to 90 g/m².

[4] The non-woven fabric according to any one of [1] to [3], wherein breaking strength by a tensile test for at least one direction in a plane direction is greater than or equal to 40 N/50 mm.

[5] The non-woven fabric according to any one of [1] to [4], wherein said crimped fibers are formed of a composite fiber in which a plurality of resins having different coefficients of thermal contraction form a phase structure and are oriented substantially parallel with a plane direction, and are crimped substantially uniformly in a thickness direction, and
said crimped fibers have a mean radius of curvature of 20 to 200 μm.

[6] The non-woven fabric according to any one of [1] to [5] that is a bandage.

Advantageous Effects of Invention

According to the present invention, it is possible to provide a stretchable non-woven fabric having little deterioration in stretching performance when used repeatedly and having excellent repetition durability. The stretchable non-woven fabric according to the present invention can be suitably used for bandages, in particular, stretchable bandages used for stopping bleeding in a wounded part or the like, and for promoting the blood flow, and other bandages for giving a pressurizing force by being wound such as a bandage for pressure therapy (pressure bandages).

DESCRIPTION OF EMBODIMENTS

Figure 1:
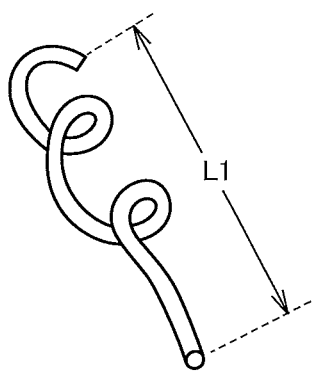
FIGS. 1(a) and 1(b) are schematic views showing a measuring method of a curvature of a fiber.
Figure 1:
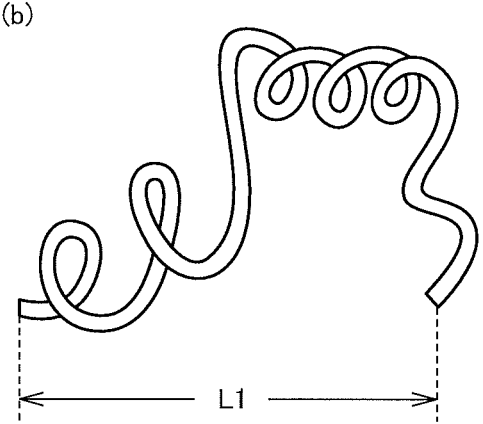
Figure 2:
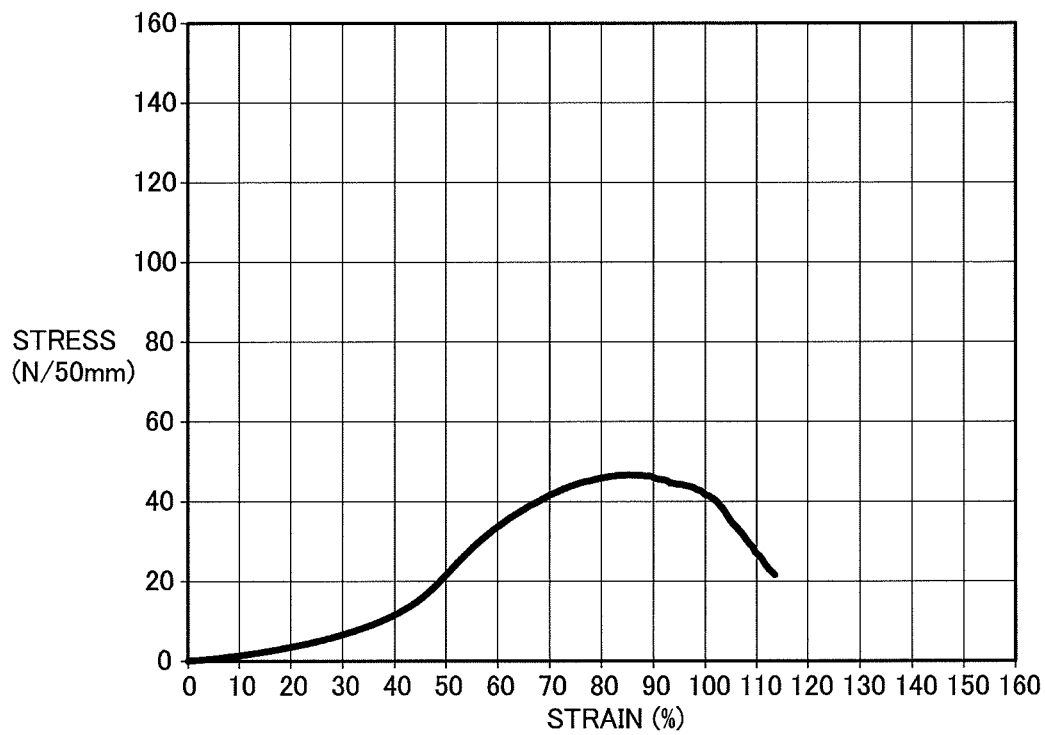
FIG. 2 is a chart showing a stress-strain curve of a stretchable non-woven fabric obtained in Example 1.
Figure 3:
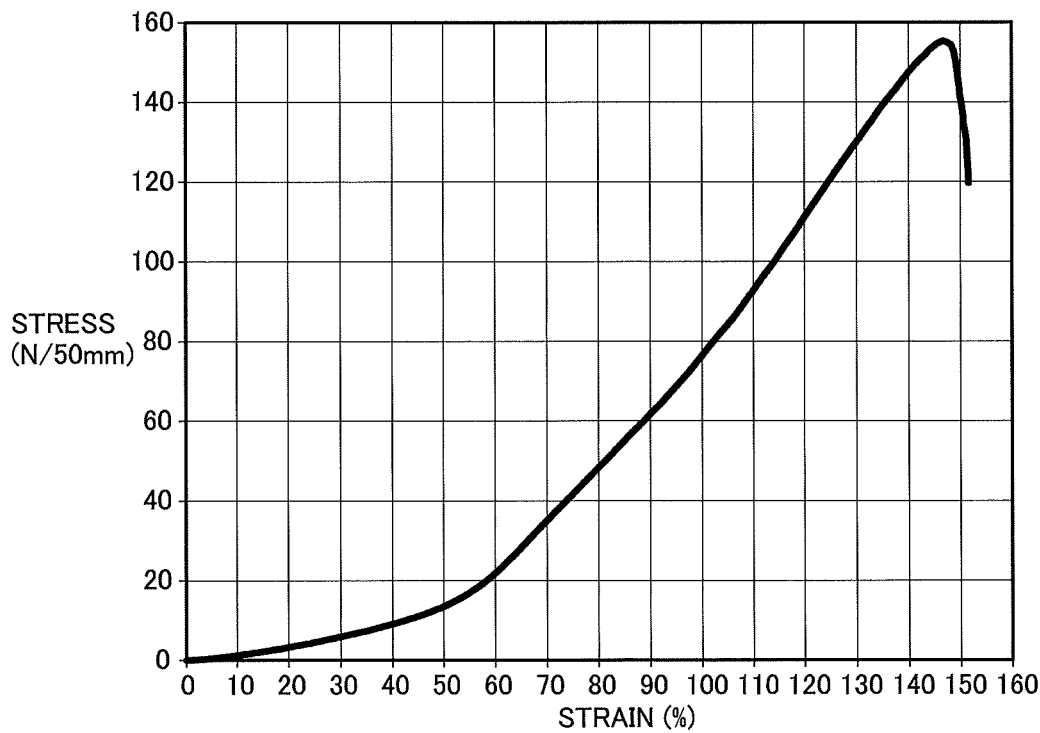
FIG. 3 is a chart showing a stress-strain curve of a stretchable non-woven fabric obtained in Example 2.
Figure 4:
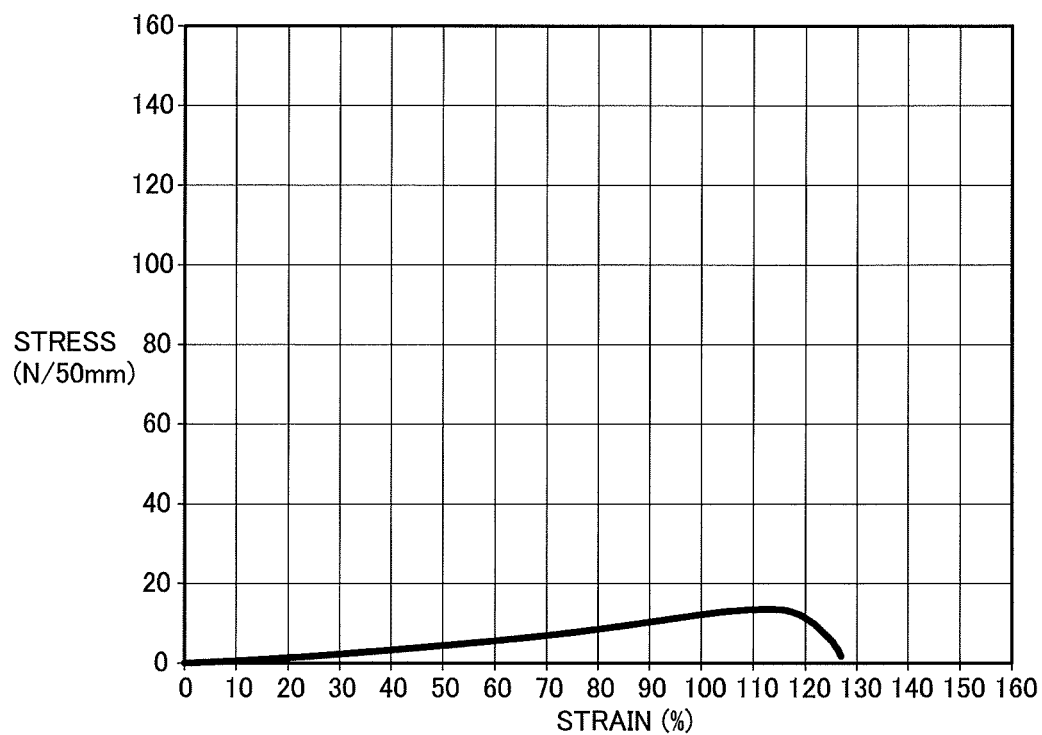
FIG. 4 is a chart showing a stress-strain curve of a stretchable non-woven fabric obtained in Comparative Example 1.
Figure 5:
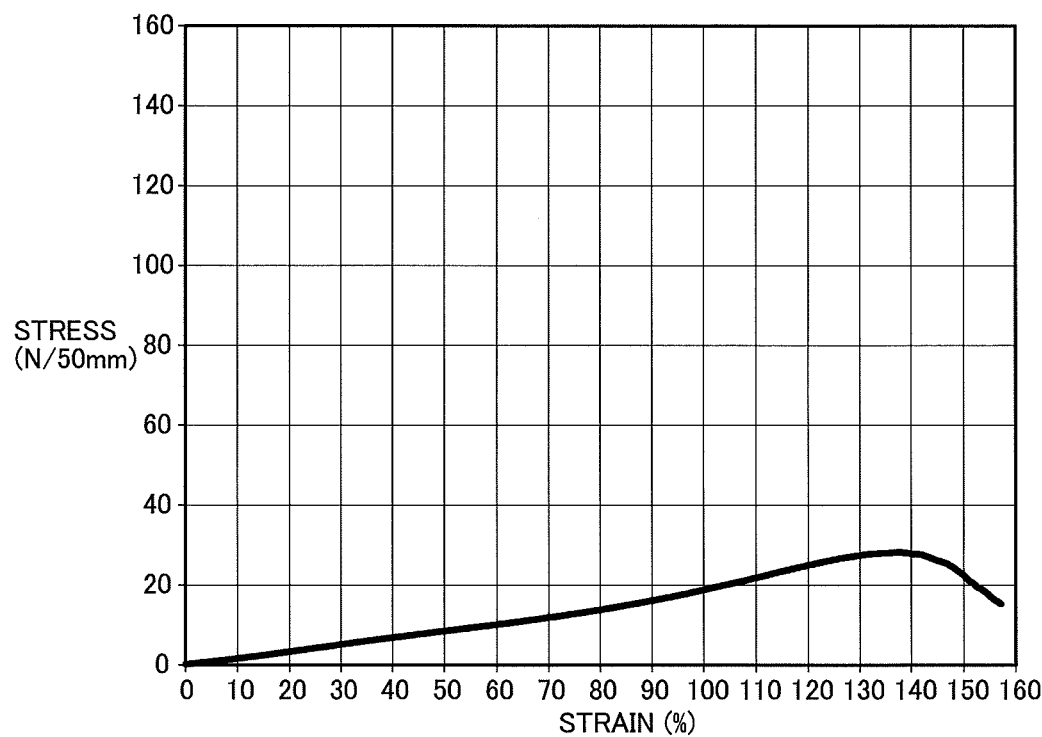
FIG. 5 is a chart showing a stress-strain curve of a stretchable non-woven fabric obtained in Comparative Example 2.
Figure 6:
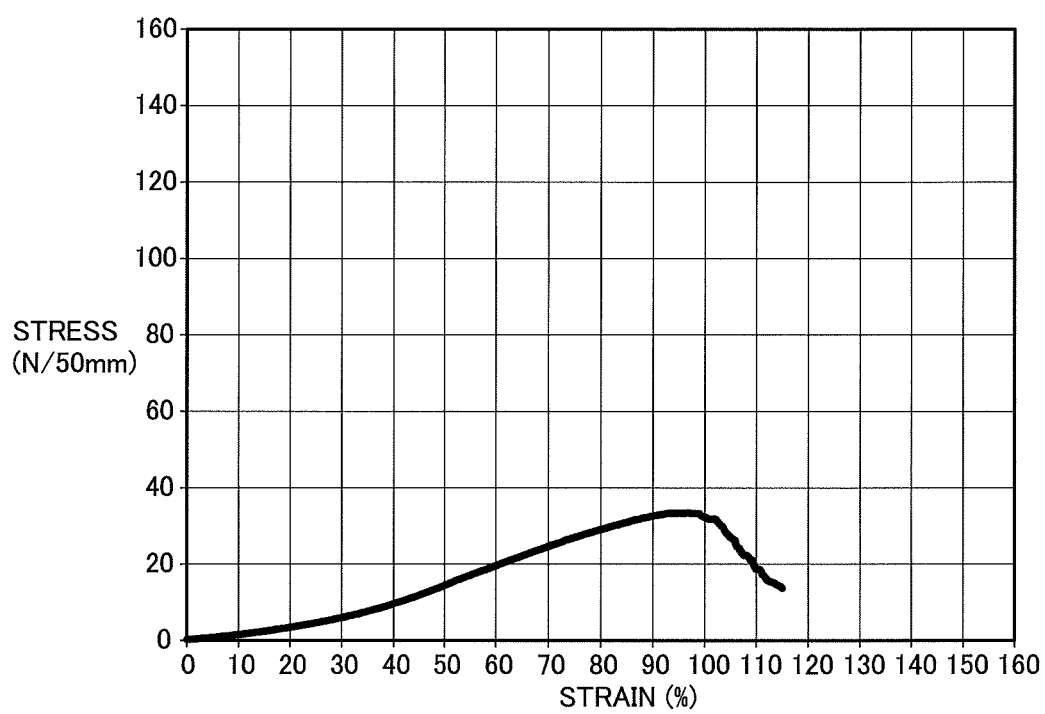
FIG. 6 is a chart showing a stress-strain curve of a stretchable non-woven fabric obtained in Comparative Example 3.

<Stretchable Non-Woven Fabric>
(1) Characteristics of Stretchable Non-Woven Fabric
The stretchable non-woven fabric according to the present invention is formed to include crimped fibers that are crimped in a coiled form as will be described later. The stretchable non-woven fabric has such a structure that individual crimped fibers forming the fabric do not substantially adhere to each other, but principally, the crimped fibers are intertwined at their crimped coil parts and thus they are restricted or latched. In the stretchable non-woven fabric according to the present invention, preferably, most (majority) of the crimped fibers (the directions of axial core of crimped fibers) forming the fabric are oriented substantially parallel with the non-woven fabric plane (the sheet plane). In the description of the present application, the expression "oriented substantially parallel with the plane direction" means a condition that a part where a large number of crimped fibers (the directions of axial core of crimped fibers) are oriented in a thickness direction locally does not exist repeatedly as is the case with intermingling by needle punching, for example.

The stretchable non-woven fabric according to the present invention preferably includes crimped fibers that are oriented in the plane direction (the longitudinal direction) thereof and crimped in a coiled form, and neighboring or crossing crimped fibers are mutually intermingled at crimpled coil parts thereof. Also in the thickness direction (or a diagonal direction) of the non-woven fabric, crimped fibers are mutually intermingled lightly. Particularly, in a fiber web, fibers are intermingled while they contract into coiled forms and the crimped fibers are restricted by intermingled crimped coil parts.

Therefore, the stretchable non-woven fabric according to the present invention extends largely in the plane direction (the longitudinal direction) by the intermingled crimped coil parts rather than in a width direction or the thickness direction. Also, in the stretchable non-woven fabric, preferably, the crimped fibers are oriented in the plane direction and in the longitudinal direction, and thus when a tension is applied in the longitudinal direction, the intermingled crimped coil parts extend, and tend to recover the original coiled forms, so that the stretchable non-woven fabric can exhibit high stretchability in the plane direction and the longitudinal direction. Further, by the light intermingling between crimped fibers in the thickness direction of the non-woven fabric, cushioning characteristics and flexibility can emerge in the thickness direction, and thus the stretchable non-woven fabric can have an excellent touch and feeling.

A crimped coil part easily intermingles with other crimped coil parts by contact under a certain degree of pressure. Therefore, the stretchable non-woven fabric according to the present invention can have excellent self-adhesiveness. In the description of the present application, "self-adhesiveness" refers to the characteristics that allow restriction or latch by joining or intermingling by contact between non-woven fabrics without use of an adhesive, a stopper or the like.

Preferably, the crimped fibers are oriented in the plane direction and the longitudinal direction, and thus when a tension is applied in the longitudinal direction, the intermingled crimped coil parts extend by elastic deformation, and when a tension is further applied, they extend by plastic deformation. In this manner, the stretchable non-woven fabric according to the present invention is able to have stretchability and self-adhesiveness with a good balance.

On the other hand, when fibers that form a non-woven fabric do not substantially adhere to each other, and there are a lot of fibers oriented in a thickness directions (a direction perpendicular to the sheet plane), these fibers also form coiled crimps, and the fibers are highly complexly intertwined. As a result, other fibers are restricted or fixed more than required, and also stretching of the crimped coil parts forming the fibers are inhibited, and thus stretchability of the non-woven fabric is deteriorated. Therefore, it is desired to orient crimped fibers parallel with the plane direction of the non-woven fabric as much as possible.

In this manner, the coiled crimped fibers are preferably oriented substantially parallel with a plane direction of the non-woven fabric according to the present invention, so that the stretchable non-woven fabric can have stretchability in the plane direction. In contrast, when the fabric is extended in the thickness direction, the fibers get loose relatively easily, so that stretchability (contraction property) as seen in the plane direction does not emerge. Such orientation of the fibers can be checked easily by observing for such stretchability even when the fibers are dense and the orientation thereof is difficult to observe visually.

The stretchable non-woven fabric according to the present invention satisfies the following formula [1]:

$$(\sigma_{65}-\sigma_{55})/(\sigma_{30}-\sigma_{20}) \geq 2.5 \qquad [1]$$

when a stress σ (N/50 mm) at a strain (elongation) of 20%, 30%, 55% and 65% in a stress-strain (S-S curve) curve for at least one direction in a plane direction, is referred to as $\sigma_{20}$, $\sigma_{30}$, $\sigma_{55}$ and $\sigma_{65}$, respectively.

The above formula [1] means showing a stress-strain curve having a stepwise inclination wherein the variation of the stress σ with respect to the variation of a certain strain (rate of change in stress) changes significantly largely at the point or the vicinity of a strains of 50%, and the ratio of the rate of change in stress on the side of the higher stress region on the basis of the rate of change in stress on the side of the lower stress region is greater than or equal to 2.5 times. Study made by the present inventors revealed that according to the non-woven fabric showing a stress-strain curve having such a stepwise inclination, deterioration in the stretching performance when used repeatedly is small (repetition durability is high), and specifically, a variation in strain in the later-described 20 N/50 mm extension repetition test can be made small. From the view point of decreasing the variation in strain in the 20 N/50 mm extension repetition test, the left-hand side of the above formula [1] is preferably greater than or equal to 2.7, more preferably greater than or equal to 2.9, further preferably greater than or equal to 3.0, particularly preferably greater than or equal to 3.5, most preferably greater than or equal to 4.0.

Stress-strain characteristics before a rate of change in stress largely changes (in a lower stress region) is mainly based on elastic deformation of a non-woven fabric, and the stress-strain characteristics after the rate of change in stress greatly changes (in a higher stress region) is mainly based on plastic deformation of the non-woven fabric. Study by the present inventors revealed that in the above formula [1] that represents the ratio of the rate of change in stress on the side of the higher stress region and the rate of change in stress on the side of the lower stress region, a larger value of the left-hand side of the above formula [1] is advantageous in decreasing a variation in strain in a 20 N/50 mm extension repetition test. In this meaning, the upper limit value of the left-hand side of the above formula [1] is not particularly limited. The left-hand side of the above formula [1] is normally less than or equal to 50, more typically less than or equal to 25.

The aforementioned "at least one direction in the plane direction" can be, for example, a machine direction (MD) in a manufacturing process, or can be a longitudinal direction for a form having a longitudinal direction, such as a bandage. The stress-strain curve is measured by a tensile test in conformity with JIS L 1913 "Test methods for nonwovens".

For achieving excellent repetition durability, in a stretchable non-woven fabric, a strain (elongation) when extended with a certain stress is preferably small in a higher stress region (a plastic deformation region) in the above stress-strain curve, and specifically, a stress $\sigma_{80}$ when a strain $\varepsilon$ (elongation) is 80% in the above stress-strain curve is preferably greater than or equal to 20 N/50 mm, more preferably greater than or equal to 30 N/50 mm, further preferably greater than or equal to 40 N/50 mm. Assuming that the above formula [1] is satisfied, the stress $\sigma_{80}$ falling within the above range makes it easy to realize a non-woven fabric exhibiting excellent repetition durability.

In the stretchable non-woven fabric according to the present invention, breaking strength for at least one direction in the plane direction is preferably greater than or equal to 40 N/50 mm, more preferably greater than or equal to 60 N/50 mm (for example, greater than or equal to 80 N/50 mm). The breaking strength falling within the above range is advantageous in improving strength, stretchability, and repetition durability of a non-woven fabric. On the other hand, when the breaking strength is excessively large, a pressurizing force is too large when the non-woven fabric is wound in the form of, for example, a bandage, and hence the breaking strength is preferably less than or equal to 200 N/50 mm, more preferably less than or equal to 180 N/50 mm. The aforementioned "at least one direction in the plane direction" is the same direction as the direction satisfying the above formula [1], and can be, for example, an MD direction, or can be a longitudinal direction for a form having a longitudinal direction, such as a bandage. The breaking strength is measured by a tensile test in conformity with JIS L 1913 "Test methods for nonwovens".

Meanwhile, breaking strength may be relatively small in a direction other than the aforementioned at least one direction in the plane direction, for example, in a direction (a CD direction) orthogonal to a machine direction (MD) of a manufacturing process, or in a width direction (a short direction) for a form having a longitudinal direction, such as a bandage, and may be, for example, 0.05 to 50 N/50 mm, preferably 0.1 to 45 N/50 mm, more preferably about 0.5 to 30 N/50 mm.

Breaking elongation for at least one direction in the plane direction is preferably greater than or equal to 90%, more preferably greater than or equal to 100%, further preferably greater than or equal to 120%. The breaking elongation falling within the above range is advantageous in improving stretchability of a non-woven fabric. When a non-woven fabric is used as a bandage, it is possible to improve a following capability when the bandage is applied to a site where its motion is large, such as a joint. Breaking elongation for the aforementioned at least one direction in the plane direction is normally less than or equal to 500%, preferably less than or equal to 350%. The aforementioned "at least one direction in the plane direction" is the same direction as the direction satisfying the above formula [1], and can be, for example, an MD direction, or can be a longitudinal direction for a form having a longitudinal direction, such as a bandage. The breaking elongation is also measured by a tensile test in conformity with JIS L 1913 "Test methods for nonwovens".

Breaking elongation in a direction other than the aforementioned at least one direction in the plane direction, for example, in a direction (a CD direction) orthogonal to a machine direction (MD) of a manufacturing process, or in a width direction (a short direction) for a form having a longitudinal direction, such as a bandage, can be, for example, 50 to 500%, preferably about 100 to 350%.

A recovery rate after 50% extension for at least one direction in the plane direction (a recovery rate after 50% extension) is preferably greater than or equal to 70% (less than or equal to 100%), more preferably greater than or equal to 80%, further preferably greater than or equal to 85%. When the extension recovery rate falls within this range, the followability to extension is improved, and for example, when the non-woven fabric is used as a bandage, it becomes possible to sufficiently follow the form of the site where it is used, and to appropriately fix and cramp by the friction between the overlapped non-woven fabrics. In particular, when several non-woven fabrics are overlapped as a result of winding, a fixing force by friction as a whole corresponds to a recovery stress, and a behavior similar to increasing a mass per unit area is exhibited. That is, in a case where the extension recovery rate is small, the non-woven fabric cannot follow a motion when a site where the fabric is used has a complicated shape or when a motion occurs in the site during use, and a part that has been deformed by the motion of the body does not recover the original condition, and fixation of the wound site is weakened. The aforementioned "at least one direction in the plane direction" is the same direction as the direction satisfying the above formula [1], and can be, for example, an MID direction, or can be a longitudinal direction for a form having a longitudinal direction, such as a bandage.

The recovery rate after 50% extension is defined by the following formula:

$$\text{Recovery rate after 50\% extension (\%)} = 100 - X$$

wherein, in a tensile test in conformity with JIS L 1913 "Test methods for nonwovens", X is a residual strain (%) after the test when a load is removed immediately after the extension percentage has reached 50%.

The recovery rate after 50% extension in a direction other than the aforementioned at least one direction in the plane direction, for example, in a direction (a CD direction) orthogonal to a machine direction (MD) of manufacturing process, or in a width direction (a short direction) for a form having a longitudinal direction, such as a bandage, can be, for example, greater than or equal to 70% (less than or equal to 100%), preferably about greater than or equal to 80%.

The stretchable non-woven fabric according to the present invention has a mass per unit area of preferably greater than or equal to 90 g/m$^2$, more preferably greater than or equal to 95 g/m$^2$. A thickness is, for example, 0.2 to 5 mm, preferably 0.3 to 3 mm, more preferably about 0.4 to 2 mm. When the mass per unit area and the thickness fall within these ranges, the balance between stretchability and flexibility (or cushioning characteristics) is excellent. Density of the stretchable non-woven fabric (bulk density) agrees with numerical values of the mass per unit area and the thickness above, and may be, for example, about 0.01 to 0.5 g/cm$^3$, more typically about 0.03 to 0.3 g/cm$^3$.

Air permeability of the stretchable non-woven fabric is greater than or equal to 0.1 cm$^3$/cm$^2$·sec, for example, 1 to 500 cm$^3$/cm$^2$·sec, preferably 5 to 300 cm$^3$/cm$^2$·sec, more preferably about 10 to 200 cm$^3$/cm$^2$·sec by air permeability according to a Frajour type method. When the air permeability falls within this range, the stretchable non-woven fabric is more suited for an application such as a bandage or the like to be used for a human body.

(2) Material and Structure of Stretchable Non-Woven Fabric

As described above, the stretchable non-woven fabric according to the present invention includes crimped fibers that are crimped in a coiled form. The crimped fibers are preferably oriented mainly in the plane direction of the non-woven fabric, and preferably crimped substantially uniformly in the thickness direction. An external shape of the stretchable non-woven fabric can be selected depending on the application purpose, and is normally a rectangular sheet shape such as a tape form or a band (long) form. The crimped fibers can be formed of a composite fiber in which a plurality of resins having different coefficients of thermal contraction (or coefficients of thermal expansion) form a phase structure.

The composite fiber forming the crimped fibers is a fiber (potential crimped fiber) having an asymmetry or layered (so-called bimetal) structure that will be crimped by heating due to a difference in coefficient of thermal contraction (or coefficient of thermal expansion) between a plurality of resins. The plurality of resins are normally different from each other in a softening point or a melting point. The plurality of resins can be selected from thermoplastic resins, for example, polyolefin resins (poly $C_{2-4}$ olefin resins and the like, such as low-density, medium-density, and high-density polyethylene, and polypropylene); acryl resins (acrylonitrile resins and the like having an acrylonitrile unit such as acrylonitrile-vinyl chloride copolymer); polyvinyl acetal resins (such as polyvinyl acetal resin); polyvinyl chloride resins (such as polyvinyl chloride, vinyl chloride-vinyl acetate copolymer, and vinyl chloride-acrylonitrile copolymer); polyvinylidene chloride resins (such as vinylidene chloride-vinyl chloride copolymer, and vinylidene chloride-vinyl acetate copolymer); styrene resins (such as high temperature polystyrene); polyester resins (poly $C_{2-4}$ alkylene arylate resins and the like, such as polyethylene terephthalate resin, polytrimethylene terephthalate resin, polybutylene terephthalate resin, and polyethylene naphthalate resin); polyamide resins (aliphatic polyamide resins such as polyamide 6, polyamide 66, polyamide 11, polyamide 12, polyamide 610, and polyamide 612, semi-aromatic polyamide resins, and aromatic polyamide resins such as polyphenylene isophthalamide, polyhexamethylene terephthalamide, and poly p-phenylene terephthalamide, and the like); polycarbonate resins (such as bisphenol A polycarbonate); polyparaphenylene benzobisoxazole resin; polyphenylene sulfide resin; polyurethane resins; cellulose resins (such as cellulose ester) and so on. Further, each of these thermoplastic resins may contain other copolymerizable units.

Among these, as the above plurality of resins, from the view point that the fibers do not melt or soften to fuse even when they are heat-treated with high-temperature water vapor, non-wet heat adhesive resins (or heat resistant hydrophobic resins or nonaqueous resins) having a softening point or a melting point of greater than or equal to 100° C., for example, polypropylene resins, polyester resins, and polyamide resins are preferred, and in particular, from the view point of an excellent balance of heat resistance, fiber formability and the like, aromatic polyester resins and polyamide resins are preferred. At least the resin that is exposed on the surface of the composite resin is preferably a non-wet heat adhesive fiber so that the composite fiber (potential crimped fiber) forming the stretchable non-woven fabric does not fuse when treated with high-temperature water vapor.

The plurality of resins forming the composite fiber are only required to have different coefficients of thermal contraction, and may be a combination of the same system of resins, or may be a combination of different systems of resins.

From the view point of adhesion, the plurality of resins forming the composite fiber are preferably a combination of the same system of resins. In a case of a combination of the same system of resins, normally, a combination of component (A) forming a homopolymer (an essential component) and component (B) forming a modified polymer (a copolymer) is used. In other words, by modifying a homopolymer that is an essential component, for example, by copolymerizing a copolymerizable monomer that decreases a degree of crystallinity, and a melting point, the softening point or the like, the resultant copolymer can have a lower degree of crystallinity than the homopolymer or can be amorphous, or can have a lower melting point, softening point or the like than the homopolymer. By changing crystallinity, a melting point or a softening point in this manner, it is possible to differentiate a coefficient of thermal contraction. The difference in melting points or softening points can be, for example, 5 to 150° C., preferably 40 to 130° C., more preferably about 60 to 120° C. The percentage of the copolymerizable monomer used for modification with respect to the total monomer is, for example, 1 to 50 mol %, preferably 2 to 40 mol %, more preferably about 3 to 30 mol % (particularly, 5 to 20 mol %). A mass ratio between a component forming the homopolymer and a component forming the modified polymer can be selected depending on the structure of fibers, and is, for example, homopolymer component (A)/modified polymer component (B)=90/10 to 10/90, preferably 70/30 to 30/70, more preferably about 60/40 to 40/60.

For ease of manufacturing of the potentially crimping composite fiber, the composite fiber is preferably a combination of aromatic polyester resins, in particular, a combination of polyalkylene arylate resin (a), and a modified polyalkylene arylate resin (b). Polyalkylene arylate resin (a) can be a homopolymer of aromatic dicarboxylic acid (symmetric aromatic dicarboxylic acid and the like, such as terephthalic acid, and naphthalene-2,6-dicarboxylic acid) and an alkane diol component ($C_{2-6}$ alkane diol and the like, such as ethylene glycol and butylene glycol). Specifically, poly $C_{2-4}$ alkylene terephthalate resins and the like, such as polyethylene terephthalate (PET) or polybutylene terephthalate (PBT) are used, and normally, PET used for a general PET fiber having an intrinsic viscosity of about 0.6 to 0.7 is used.

On the other hand, in modified polyalkylene arylate resin (b), a copolymerizing component that decreases the melting point or the softening point, and the crystallinity of polyalkylene arylate resin (a) that is an essential component includes, for example, a dicarboxylic acid component such as asymmetric aromatic dicarboxylic acid, alicyclic dicarboxylic acid, and aliphatic dicarboxylic acid, and an alkane diol component having a longer chain length than the alkane diol of polyalkylene arylate resin (a) and/or an ether bond-containing diol component. The copolymerizing component can be used solely or in combination of two or more kinds. Among these components, as a dicarboxylic acid component, asymmetric aromatic dicarboxylic acids (such as isophthalic acid, phthalic acid, and sodium 5-sulfoisophthalate), aliphatic dicarboxylic acids ($C_{6-12}$ aliphatic dicarboxylic acid and the like, such as adipic acid) and the like are commonly used, and as a diol component, alkane diols ($C_{3-6}$ alkane diols and the like, such as 1,3-propanediol, 1,4-butanediol, 1,6-hexanediol, and neopentyl glycol), polyoxyalkylene glycols (polyoxy $C_{2-4}$ alkylene glycols and the like, such as diethylene glycol, triethylene glycol, polyethylene glycol, and polytetramethylene glycol) and the like are commonly used. Among these, asymmetric aromatic dicarboxylic acids such as isophthalic acid, polyoxy $C_{2-4}$ alkylene glycols and the like, such as diethylene glycol are preferred.

Further, modified polyalkylene arylate resin (b) may be an elastomer made up of a $C_{2-4}$ alkylene arylate (such as ethylene terephthalate and butylene terephthalate) as a hard segment, and a (poly)oxyalkylene glycol or the like as a soft segment.

In modified polyalkylene arylate resin (b), the percentage of the dicarboxylic acid component (such as, for example, isophthalic acid) for decreasing a melting point or a softening point, relative to the total amount of the dicarboxylic acid component forming modified polyalkylene arylate resin (b) is, for example, 1 to 50 mol %, preferably 5 to 50 mol %, more preferably about 15 to 40 mol %. The percentage of the diol component (such as, for example, ethylene glycol) for decreasing a melting point or a softening point, relative to the total amount of the diol component forming modified polyalkylene arylate resin (b) is, for example, less than or equal to 30 mol %, preferably less than or equal to 10 mol % (for example, about 0.1 to 10 mol %). If the percentage of the copolymerizing component is too low, sufficient crimps do not emerge, and shape stability and stretchability of the non-woven fabric after emergence of crimps are deteriorated. On the other hand, if the percentage of the copolymerizing component is too high, crimp emerging performance is high, but it becomes difficult to conduct spinning stably.

Modified polyalkylene arylate resin (b) may contain a polyvalent carboxylic acid component such as trimellitic acid or pyromellitic acid, a polyol component such as glycerin, trimethylolpropane, trimethylolethane or pentaerythritol, and the like as a monomer component as is necessary.

A shape of a cross section of the composite fiber (a shape of a section perpendicular to the longitudinal direction of a fiber) may be a hollow section shape without being limited to a round section or variant sections [such as flat, elliptical, polygonal, 3 to 14-foiled, T-shape, H-shaped, V-shaped, and dog-bone-like (I-shaped) sections] that are general solid section shapes, but the composite fiber normally has a round section.

As a structure of the cross section of the composite fiber, a phase structure formed by a plurality of resins, for example, structures of a core-clad type, a sea-island type, a blend type, a parallel type (a side-by-side type or a multi-layer bonding type), a radial type (a radial bonding type), a hollow radial type, a block type, a random composite type and the like can be recited. Among these, a structure in which phase parts neighbor (a so-called bimetal structure) and a structure in which a phase structure is asymmetric, for example, an eccentric core-clad type structure or parallel type structure is preferred for ease of causing emergence of self-crimping by heating.

When the composite fiber has a core-clad type structure such as an eccentric core-clad type, a core part may be formed of a wet heat adhesive resin (for example, vinyl alcohol polymers or the like, such as ethylene-vinyl alcohol copolymer and polyvinyl alcohol), or a thermoplastic resin having a low melting point or softening point (for example, polystyrene, low-density polyethylene or the like) insofar as the fiber has a difference in thermal contraction with non-wet heat adhesive resin of a clad part situated on the surface, and is crimpable.

A mean fineness of the composite fiber can be selected, for example, from a range of about 0.1 to 50 dtex, and is preferably 0.5 to 10 dtex, more preferably about 1 to 5 dtex (particularly, 1.5 to 3 dtex). If the fineness is too small, it becomes difficult to manufacture a fiber itself, and additionally it is difficult to ensure strength of the fiber. Also in a step of causing emergence of crimps, it becomes difficult to allow emergence of neat coiled crimps. On the other hand, if the fineness is too large, a fiber becomes rigid, and sufficient crimps are difficult to emerge.

A mean fiber length of the composite fiber can be selected, for example, from a range of about 10 to 100 mm, and is preferably 20 to 80 mm, more preferably about 25 to 75 mm (particularly 40 to 60 mm). If the fiber length is too short, it becomes difficult to form a fiber web, and also intermingling between crimped fibers is insufficient when crimps are caused to emerge, so that it becomes difficult to ensure strength and stretchability of the non-woven fabric. If the fiber length is too large, it becomes difficult to form a fiber web of a uniform mass per unit area, and also intermingling between fibers frequently emerges at the point of time of web formation, and the fibers interfere with each other in emergence of crimps to make emergence of stretchability difficult. When the mean fiber length falls within the above range, part of the fibers crimped on the surface of the stretchable non-woven fabric are exposed appropriately on the surface of the non-woven fabric, so that it is possible to improve self-adhesiveness of the stretchable non-woven fabric.

The above composite fiber is a potential crimped fiber, and by subjecting the composite fiber to a heat treatment, crimps emerge (or appear), and the composite fiber becomes a fiber having substantially coiled (spiral or helical spring) spatial crimps.

The number of crimps before heating (machine crimp number) is, for example, 0 to 30 crimps/25 mm, preferably 1 to 25 crimps/25 mm, more preferably about 5 to 20 crimps/25 mm. The number of crimps after heating is, for example, greater than or equal to 30 crimps/25 mm (for example, 30 to 200 crimps/25 mm), preferably 35 to 150 crimps/25 mm, more preferably about 40 to 120 crimps/25 mm, and may be about 45 to 120 crimps/25 mm (in particular, 50 to 100 crimps/25 mm).

In the stretchable non-woven fabric according to the present invention, it is preferred that the crimped fibers are crimped substantially uniformly in the thickness direction, in other words, crimps of the composite fiber emerge substantially uniformly in the thickness direction. Specifically, in a center part (an internal layer) of regions obtained by dividing into three equal parts in the thickness direction in a cross section in the thickness direction, the number of fibers forming a coiled crimp of one round or more is preferably 5 to 50 fibers/5 mm (length in the plane direction)·0.2 mm (thickness), more preferably 10 to 50 fibers/5 mm (plane direction)·0.2 mm (thickness), further preferably 20 to 50 fibers/5 mm (plane direction)·0.2 mm (thickness). Since axes of most of the crimped fibers are oriented substantially parallel with the plane direction, and the number of crimps is substantially uniform in the thickness direction, high stretchability is realized even though a rubber or an elastomer is not contained, and practical strength can be imparted even though an adhesive is not contained. By the wording "regions obtained by dividing into three equal parts in the thickness direction" used in the description of the present application, each region obtained by slicing into three equal parts in the direction orthogonal to the thickness direction of the stretchable non-woven fabric is referred.

The uniformity of the crimps in the thickness direction can also be evaluated by the uniformity of the curvature of fiber. The curvature of fiber means a ratio (L2/L1) of fiber length (L2) to distance (L1) between both ends of a crimped fiber, and the curvature of fiber (in particular, the curvature of fiber in the middle region in the thickness direction) is, for example, greater than or equal to 1.3 (for example, 1.35 to 20), preferably 2 to 10 (for example, 2.1 to 9.5), more preferably about 4 to 8 (in particular, 4.5 to 7.5). As will be described later, since the curvature of fiber is measured based on an electron microphotograph of the section of the stretchable non-woven fabric, fiber length (L2) does not mean a fiber length (an actual length) of a three-dimensionally crimped fiber in an extended and straightened condition, but means a fiber length (a fiber length in the photograph) of a two-dimensionally crimped fiber in an extended and straightened condition on the photograph. Therefore, fiber length (L2) is measured to be smaller than the actual fiber length.

When crimps emerge substantially uniformly in the thickness direction, the curvature of fiber is uniform in the thickness direction. The uniformity of the curvature of fiber can be evaluated by comparison of curvature of fiber among individual layers obtained by dividing into three equal parts in the thickness direction in the section of the thickness direction. In other words, in the section of the thickness direction, the curvature of fiber in each region obtained by dividing into three equal parts in the thickness direction falls within the above range, and a percentage of the minimum value to the maximum value of the curvature of fiber in each region (percentage of the region where the curvature of fiber is minimum to the region where the curvature of fiber is maximum) is, for example, greater than or equal to 75% (for example, 75 to 100%), preferably 80 to 99%, more preferably about 82 to 98% (in particular, 85 to 97%).

As a specific measuring method for the curvature of fiber and the uniformity thereof, a method of imaging a section of the stretchable non-woven fabric by an electron microphotograph, and measuring the curvature of fiber for a region selected from the individual regions obtained by dividing into three equal parts in the thickness direction is employed. A region to be measured is a region of greater than or equal to 2 mm in the longitudinal direction for each layer of a front layer (a front region), an internal layer (a middle region), and a back layer (a back region) obtained by dividing into three equal parts. The thickness direction of each measurement region is set in such a manner that each measurement region has the same extension of thickness near the center of each layer. Also each measurement region is set to contain greater than or equal to 100 (preferably greater than or equal to 300, more preferably about 500 to 1000) fiber fragments that are parallel in the thickness direction and for which curvature of fiber can be measured in each measurement region. After setting each of these measurement regions, the curvature of fiber of every fiber in the region is measured, and a mean value is calculated for each measurement region, and then uniformity of the curvature of fiber is calculated by comparing the region showing the maximum mean value and the region showing the minimum mean value.

The crimped fibers forming the stretchable non-woven fabric have substantially coiled crimps after emergence of crimps as described above. The mean radius of curvature of a circle formed by a coil of the crimped fiber can be selected, for example, from the range of about 10 to 250 µm, and is preferably 20 to 200 µm (for example, 50 to 200 µm), more preferably 50 to 160 µm (for example, 60 to 150 µm), further preferably about 70 to 130 µm. The mean radius of curvature is an index indicating the mean size of the circles formed by the coils of the crimped fibers, and a large value of the mean radius of curvature means that the formed coil has a loose shape, or in other words, the col has a shape having a small number of crimps. The coil having a small number of crimps is disadvantageous for emergence of sufficient stretching performance because intermingling between crimped fibers is reduced, and shape recovery for a deformed coil shape becomes difficult. When the mean radius of curvature is too small, intermingling between crimped fibers is not insufficient, and it becomes difficult to ensure web strength. In such a case, a stress at the time of deformation of the shape of the coil is too large, and breaking strength is excessively large, so that it becomes difficult to obtain appropriate stretchability, or a pressurizing force when wound, for example, as a bandage is too large.

The mean pitch (mean crimping pitch) of a coil in the crimped fibers is, for example, 0.03 to 0.5 mm, preferably 0.03 to 0.3 mm, more preferably about 0.05 to 0.2 mm. If the mean pitch is excessively large, the number of coiled crimps that can emerge per one fiber fragment is small, and sufficient stretchability cannot be exerted. If the mean pitch is excessively small, intermingling between crimped fibers is not sufficient, and it becomes difficult to ensure strength of the non-woven fabric.

The stretchable non-woven fabric (a fiber web) may contain other fiber (non-composite fiber) in addition to the above composite fiber. The non-composite fiber includes, for example, besides the aforementioned fibers formed of a non-wet heat adhesive resin or a wet heat adhesive resin, cellulose fibers [such as, for example, natural fibers (cotton, wool, silk, linen, and the like), semisynthetic fibers (acetate fibers such as triacetate fiber), regenerated fibers (rayon, polynosic, cupra, Lyocell (such as, for example, registered tradename: "Tencel", and the like))]. The mean fineness and the mean fiber length of the non-composite fiber are similar to those of the composite fiber. The non-composite fiber can be used solely or in combination of two or more kinds. Among these, regenerated fibers such as rayon, semisynthetic fibers such as acetate, polyolefin fibers such as polypropylene fiber or polyethylene fiber, polyester fibers, polyamide fibers and the like are preferred. In particular, from the view point of blendability or the like, a fiber of the same type as the composite fiber is preferred, and, for example, when the composite fiber is a polyester fiber, the non-composite fiber can also be a polyester fiber.

The ratio between the composite fiber and the non-composite fiber (the mass ratio) can be selected from a range of about composite fiber/non-composite fiber=50/50 to 100/0, and is, for example, 60/40 to 100/0 (for example, 60/40 to 99.5/0.5), preferably 70/30 to 100/0 (for example, 70/30 to 99.5/0.5), more preferably 80/20 to 100/0 (for example, 80/20 to 99.5/0.5), further preferably 90/10 to 100/0 (for example, 90/10 to 99.5/0.5), particularly preferably about 95/5 to 100/0. By cotton blending of the non-composite fiber, it is possible to adjust a balance of strength and stretchability or flexibility of the stretchable non-woven fabric. However, if the proportion of the composite fiber is too small, in stretching of the composite fiber after emergence of crimps, in particular, in contraction of the composite fiber after extension, the non-composite fiber resists the contraction, so that recovery of the shape of the stretchable non-woven fabric becomes difficult.

The stretchable non-woven fabric (a fiber web) may contain commonly used additives, for example, stabilizers (a heat stabilizer such as a copper compound, an ultraviolet absorber, a light stabilizer, an antioxidant, and the like), antibacterial agents, deodorizing agents, perfumes, coloring agents (dyes, pigments and the like), fillers, antistatic agents, flame retarders, plasticizers, lubricants, crystallization speed retarders and so on. The additive can be used solely or in combination of two or more kinds. The additive may be carried on the surface of the fibers, or can be contained in the fibers.

<Method for Producing Stretchable Non-Woven Fabric>

The stretchable non-woven fabric according to the present invention can be desirably produced by a method including a step of webbing fibers including the composite fiber (a potential crimped fiber) (a webbing step), a step of entangling the fibers in a composite fiber web (an entangling step), and a step of heating the composite fiber web to crimp the composite fiber (a heating step).

As a method for forming a fiber web in the webbing step, commonly used methods, for example, direct methods such as a span bond method, and a melt blow method, a carding methods using melt-blown fibers, staple fibers or the like, and a dry method such as an airlaying method, and the like can be employed. Among these, a carding method using melt-blown fibers or staple fibers, in particular, a carding method using staple fibers is generally used. Examples of webs obtained by using staple fibers include a random web, a semi-random web, a parallel web, and a cross lap web and the like.

Then, at least part of the fibers in the obtained fiber web is entangled (the entangling step). By conducting the entangling step, it is possible to obtain a non-woven fabric in which crimped fibers are appropriately intermingled in the next heating step. The entangling method may be a method of mechanically entangling, but a method of entangling by spraying or injecting (blowing) water is preferred. Entangling the fibers by water flow increases the density of intermingling by crimping in the heating step, and makes the fiber web into a wet state, and allows more uniform transmission of water vapor inside the fiber web, and thus is advantageous in obtaining a non-woven fabric having excellent repetition durability. Water to be sprayed or injected may be sprayed from one side of the fiber web, or may be sprayed from both sides, however, from the view point of effectively conducting strong intermingling, water is preferably sprayed from both sides.

The jet pressure of the water in the entangling step is, for example, greater than or equal to 2 MPa (for example, 2 to 15 MPa), preferably 3 to 12 MPa, more preferably about 4 to 10 MPa (in particular, 5 to 8 MPa) so that the fiber intermingling falls within an appropriate range. The temperature of the water to be sprayed or injected is, for example, 5 to 50° C., preferably 10 to 40° C., for example, about 15 to 35° C. (a normal temperature).

As a method for spraying or injecting water, a method of injecting water by using a nozzle or the like having a regular spraying area or spraying pattern is preferred from the view point of convenience or the like. Specifically, water can be injected to a fiber web that is transferred by a belt conveyer in a condition where the fiber web is placed on the conveyer belt. The conveyer belt may be water-permeable, and also water may be injected to the fiber web through the water-permeable conveyer belt from the back side of the fiber web. In order to control scattering of fibers by injection of water, the fiber web may be moistened in advance with a small amount of water.

In the nozzle for spraying or injecting water, a plate or a die in which predetermined orifices are successively arranged in the width direction can be used and arranged so that the orifices are aligned in the width direction of the fed fiber web. As the orifice line, at least one line is required, and a plurality of lines may be arranged in parallel. Also, a plurality of nozzle dies each having one line of orifices may be installed in parallel.

In the case of using a nozzle of a type in which a plate is punched to give orifices, the thickness of the plate can be about 0.5 to 1.0 mm. The diameter of an orifice is normally 0.01 to 2 mm, preferably 0.05 to 1.5 mm, more preferably about 0.1 to 1.0 mm. The pitch of orifices is normally 0.1 to 2 mm, preferably 0.2 to 1.5 mm, more preferably about 0.3 to 1 mm.

While the belt conveyer used herein is not particularly limited insofar as it is basically able to convey a fiber web without disturbing the form of the fiber web, an endless conveyer is desirably used. Only one belt conveyer may be used solely, or another belt conveyer may be combined as is necessary, and a fiber web may be conveyed while it is sandwiched between these belts. In particular, in the next heating step for fixing the fiber web in the final form, the fiber web may be sandwiched between a set of belts, and the density of the fiber web may be adjusted. By conveying in this manner, it is possible to prevent the form of the conveyed web from being deformed by water for entangling, high-temperature water vapor in the heating step, and external force such as oscillation of the conveyer in treating the fiber web. When one set of belts is used, the distance between the belts can be appropriately selected according to a mass per unit area and a density of a desired fiber web, and is, for example, 1 to 10 mm, preferably 1 to 8 mm, more preferably about 1 to 5 mm.

An endless belt used in a conveyer is not particularly limited insofar as it does not interfere conveyance of the fiber web, water for entangling, and a high-temperature water vapor treatment in the heating step, and when it is a net, a net that is coarser than approximately 90 mesh (for example, a net of about 10 to 80 mesh) is preferred. A net with finer mesh has poor air permeability, so that water for entangling and water vapor in the next step become difficult to permeate. While a material of a belt is not particularly limited, as the material of the belt used in the heating step, metal, thermo-protected polyester resins, heat resistant resins such as polyphenylene sulfide resins, polyarylate resins (wholly aromatic polyester resins), and aromatic polyamide resins and the like are preferred from the view point of heat resistance against the water vapor treatment, and the like. While a belt used in a conveyer may be the same in the entangling step by water flow or the like, and in the heating step by high-temperature water vapor, normally separated different conveyers are used because adjustment is required in each step.

It is preferred to provide a step of making fibers in the fiber web localized in a plane (a localizing step) prior to the above entangling step. By conducting this step, a region where the fiber density is low is formed in the fiber web, so that it is possible to efficiently inject the water flow inside the fiber web in the case where the entangling step is water flow entangling, and it becomes easy to realize appropriate intermingling not only on the surface of the fiber web but also inside the fiber web. By conducting this localizing step, it becomes easy to obtain the non-woven fabric satisfying the above formula [1].

The localizing step can be conducted by spraying or injecting low-pressure water to the fiber web. The low-pressure water may be sprayed or injected to the fiber web continuously, but is preferably sprayed intermittently or periodically. By spraying water intermittently or periodically to the fiber web, it is possible to form a plurality of low-density parts and a plurality of high-density parts alternately and periodically.

The ejection pressure of water in this localizing step is preferably as low as possible, and is, for example, 0.1 to 1.5

MPa, preferably 0.3 to 1.2 MPa, more preferably about 0.6 to 1.0 MPa. The temperature of water to be sprayed or injected is, for example, 5 to 50° C., preferably 10 to 40° C., for example, about 15 to 35° C. (normal temperature).

A method for spraying or injecting water intermittently or periodically is not particularly limited insofar as the method enables periodic and alternate formation of the gradient of the density in the fiber web, however, from the view point of convenience or the like, a method of spraying water through a plate-like object (a porous plate or the like) having a regular spraying region or a spraying pattern formed by a plurality of pores is preferred.

Specifically, the fiber web obtained in the webbing step is fed to the next step by a belt conveyer, and then the fiber web may be allowed to pass between a drum formed of a porous plate (a porous plate drum) and a belt in the condition where it is placed on the conveyer belt. The conveyer belt may be water-permeable, and when the fiber web passes between the porous plate drum and the belt, water can be ejected in a spray form with the above pressure so that the water passes the conveyer belt through the fiber web from inside the drum. In this manner, the fibers forming the fiber web on the conveyer belt can be moved to a non-spraying area where no pore of the porous plate is allocated, so that it is possible to reduce the fiber quantity of the site to which a porous is allocated.

While the arrangement or the arrangement structure of the pores of the porous plate is not particularly limited, it may have, for example, a structure in which pores are arranged alternately in a net or grid (hound's tooth check) pattern. The pore diameter of each pore is normally identical, and is, for example, 1 to 10 mm, preferably about 1.5 to 5 mm. The pitch between neighboring pores is also normally identical, and is, for example, 1 to 5 mm, preferably about 1.5 to 3 mm.

If the pore diameter is too small, the amount of flowing water is reduced, and there arises a case where the fibers of the fiber web cannot be moved. On the other hand, if the pore diameter is too large, the necessity of increasing the pitch arises for ensuring the shape of the drum, and as a result, there arises a part where water does not come into contact with the fiber web. This can raise quality unevenness or difficulty of conducting a uniform treatment. If the pitch of pores is too small, the necessity of decreasing the pore diameter inevitably arises, and the water amount cannot be no longer ensured. Contrarily, if the pitch is too large, a part where water does not come into contact with the fiber web arises, and quality unevenness is likely to occur.

The fiber web in which fibers are appropriately entangled is fed to the next step by the belt conveyer, and crimped by heating with high-temperature water vapor. In the method of treating with high-temperature water vapor, the fiber web fed by the belt conveyer is exposed to a high-temperature or superheated steam (high pressure steam) flow to render the composite fiber (a potential crimped fiber) emerge coiled crimps, and thus the stretchable non-woven fabric is obtained. In other words, by emergence of crimps, the composite fiber moves while its form is changed to a coiled form, and three-dimensional intermingling among fibers emerges. Since the fiber web has air permeability, the high-temperature water vapor penetrates inside even if the treatment is conducted from one direction, and crimps that are substantially uniform in the thickness direction emerge, and fibers are intermingled uniformly.

Specifically, the fiber web after the entangling step is subjected to a treatment with high-temperature water vapor on the belt conveyer, and the fiber web contracts simultaneously with the high-temperature water vapor treatment. Therefore, it is desired that the fiber web to be fed is overfed in accordance with an areal contraction coefficient of an intended non-woven fabric directly before exposure to high-temperature water vapor. The rate of overfeeding is 110 to 300%, preferably about 120 to 250% relative to the length of the intended non-woven fabric.

For supplying the fiber web with water vapor, a commonly used water-vapor injecting device is used. As the water-vapor injecting device, a device capable of spraying water vapor at a desired pressure and in a desired amount over the entire width of the fiber web almost uniformly is preferred. When a combination of two belt conveyers is used, a water-vapor injecting device is attached in one conveyer, and water vapor is supplied to the fiber web through a water-permeable conveyer belt, or through a conveyer net placed on the conveyer. A suction box may be attached to the other conveyer. While excessive water vapor having passed the fiber web may be sucked and discharged by the suction box, it is preferred to supply water vapor without being sucked and discharged by the suction box because the fiber web is required to be kept in a free state as much as possible so as to bring water vapor into contact with the fiber web sufficiently and to make fiber crimps emerge by this heat more efficiently. For conducting the water-vapor treatment on both the front and the back sides of the fiber web at once, another water-vapor injecting device may be installed in the conveyer of the downstream side than the site where the above water-vapor injecting device is attached in the conveyer opposite to the conveyer to which the above water-vapor injecting device is attached. When one wants to treat both the front and the back sides of the non-woven fabric with water vapor in the case where the water-vapor injecting device on the downstream side is absent, the fiber web being once treated may be passed again in the treating device after the fiber web is turned over, as an alternative.

Since high-temperature water vapor injected from the water-vapor injecting device is an airflow, it enters inside the fiber web without significantly moving the fibers in the fiber web that is an object to be treated unlike cases of a water flow entangling treatment or a needle punching treatment. It is considered that by the entry action of the water vapor flow into the fiber web, the water vapor flow efficiently covers the surface of each fiber existing in the fiber web, and enables uniform thermal crimping. Also since heat can be conducted inside the fiber web sufficiently, as compared with a dry heat treatment, the degree of crimping is almost uniform in the plane direction and the thickness direction.

Also as a nozzle for injecting high-temperature water vapor, likewise the above nozzle for water flow entangling, a plate or a die in which predetermined orifices are successively arranged in the width direction can be used and arranged so that the orifices are aligned in the width direction of the fed fiber web. As the orifice line, at least one line is required, and a plurality of lines may be arranged in parallel. Also, a plurality of nozzle dies each having one line of orifices may be installed in parallel.

In the case of using a nozzle of a type in which a plate is punched to give orifices, the thickness of the plate may be about 0.5 to 1.0 mm. While the diameter and the pitch of orifices are not particularly limited insofar as emergence of intended crimps and fiber intermingling in association with this emergence can be efficiently achieved, the diameter of an orifice is normally 0.05 to 2 mm, preferably 0.1 to 1 mm, more preferably about 0.2 to 0.5 mm. The pitch of orifices is normally 0.5 to 5 mm, preferably 1 to 4 mm, more preferably about 1 to 3 mm. If the diameter of the orifice is too small, an operational problem of easily clogging is likely to occur. Contrarily, if it is too large, it becomes difficult to obtain a sufficient water vapor injecting force. On the other hand, if the pitch is too small, the pore diameter is also small, and the amount of high-temperature water vapor decreases. On the other hand, if the pitch is too large, it becomes difficult to ensure strength because there arises a case where high-temperature water vapor fails to hit the fiber web sufficiently.

Also the high-temperature water vapor to be used is not particularly limited insofar as emergence of intended fiber crimps and appropriate fiber intermingling in association with this can be achieved, and can be set according to the quality of material and form of the fiber to be used, and the pressure is, for example, 0.1 to 2 MPa, preferably 0.2 to 1.5 MPa, more preferably about 0.3 to 1 MPa. If the pressure of the water vapor is too high, the fibers forming the fiber web can move more than required to cause disturbance of the formation, or the fibers can be intermingled more than required. In an extreme case, the fibers are fused together, and it becomes difficult to ensure stretchability. Further, when the pressure is too weak, it becomes impossible to give the quantity of heat that is required for emergence of crimps of fibers to the fiber web, or the water vapor cannot penetrate the fiber web and emergence of crimps of fibers in the thickness direction tends to be nonuniform. Also it is difficult to control the uniform ejection of the water vapor from the nozzle.

The temperature of the high-temperature water vapor is, for example, 70 to 150° C., preferably 80 to 120° C., more preferably about 90 to 110° C. The treatment speed with high-temperature water vapor is, for example, less than or equal to 200 m/minutes, preferably 0.1 to 100 m/minute, more preferably about 1 to 50 m/minute.

After causing emergence of crimps of the composite fiber in the fiber web in the manner as described above, there is sometimes a case where water remains in the non-woven fabric, and hence, the non-woven fabric may be dried as is necessary. Regarding the drying, it required that the fibers on the surface of the non-woven fabric being in contact with the heater for drying will not be fused by the heat for drying to deteriorate stretchability, and a commonly used method can be employed insofar as stretchability can be maintained. While large-sized drying equipment such as a cylinder dryer, a tenter or the like used for drying non-woven fabrics may be used, it is preferred to use non-contact methods such as infrared radiation, microwave radiation, and electron beam radiation, a method of blowing hot air, a method of passing in hot air and the like because the remaining water is very small in amount, and is often in such a level that can be dried by relatively light drying means.

The obtained non-woven fabric is wetted with water in its manufacturing process, and exposed under a high-temperature water vapor atmosphere. In other words, in the non-woven fabric of the present invention, since the non-woven fabric itself experiences a treatment similar to laundry, the extraneous matters adhered to the fibers such as fiber spinning oil are washed out. Therefore, the stretchable non-woven fabric of the present invention is hygienic and exhibits high water repellency.

EXAMPLES

Hereinafter, the present invention will be described more specifically by way of examples, however, it is to be noted that the present invention is not limited by these examples.

Physical property values in the following Examples and Comparative Examples were measured by the following methods.

[1] Machine Crimp Number

Measurement was conducted in conformity with JIS L 1015 "Test methods for man-made staple fibers" (8.12.1).

[2] Mean Number of Coiled Crimps

From a non-woven fabric, a crimped fiber (composite fiber) was pulled out with care so as not to extend the coiled crimp, and measurement was conducted in conformity with JIS L 1015 "Test methods for man-made staple fibers" (8.12.1) as with the measurement of the machine crimp number. This measurement was conducted only for a fiber in which coiled crimps emerge.

[3] Mean Crimping Pitch

At the time of measuring the mean number of coiled crimps, a distance between successively neighboring coils was measured, and a mean crimping pitch was shown as a mean value of n=100.

[4] Mean Radius of Curvature

Using a scanning electron microscope (SEM), a photograph of an arbitrary section of the non-woven fabric, enlarged 100 times was taken. Among the fibers in the photograph of the non-woven fabric section thus taken, for a fiber that forms a spiral (coil) of one or more rounds, the radius of a circle when the circle is described along the spiral (radius of the circle when the crimped fiber is observed in the coil axial direction) was determined as a radius of curvature. When a fiber describes a spiral ovally, ½ of the sum of the major axis and the minor axis of the oval was determined as a radius of curvature. However, for excluding the case where sufficient coiled crimps do not emerge in the crimped fiber, or the case where the spiral form of the fiber is seen as an oval because it is observed diagonally, only the ovals having a ratio between the major axis and the minor axis of the oval falls within the range of 0.8 to 1.2 were selected as objects to be measured. The mean radius of curvature was determined as a mean value of n=100.

[5] Curvature of Fiber and Uniformity of Crimped Fibers (Composite Fiber)

An electron microphotograph (magnification: 100-power) in an arbitrary section of a non-woven fabric was taken, and in the part where the photographed fibers can be seen, the part was divided into three equal regions: a front layer, an internal layer, and a back layer in the thickness direction, and a measurement region was set in the vicinity of the center of each layer in such a manner that 500 or more crimped fibers that are greater than or equal to 2 mm in the longitudinal direction and measurable are contained. For these regions, an end-to-end distance (shortest distance) between one end and the other end of the crimped fiber was measured, and further, the fiber length (fiber length on the photograph) of the crimped fiber was measured. That is, when an end of a crimped fiber is exposed on the surface of the non-woven fabric, the end is directly regarded as an end for measuring an end-to-end distance, and when an end is buried inside the non-woven fabric, the boundary part at which the fiber is buried inside the non-woven fabric (end on the photograph) is regarded as an end for measuring an end-to-end distance. Among the crimped fibers photographed at this time, the fiber image for which continuity of greater than or equal to 100 μm could not be recognized was excluded from objects to be measured. From a ratio (L2/L1) of fiber length (L2) of the composite fiber to the end-to-end distance (L1), a curvature of fiber was calculated. A mean value of the curvature of fiber was calculated for each of the front layer, the internal layer, and the back layer obtained by dividing into three equal parts in the thickness direction, and further from the ratio between the maximum value and the minimum value of each layer, the uniformity of the curvature of fiber in the thickness direction was calculated.

FIGS. 1(a) and 1(b) show schematic views about the method for measuring a curvature of fiber of a photographed crimped fiber. FIG. 1(a) shows a crimped fiber in which one end is exposed to the surface, and the other end is buried inside the non-woven fabric, and in this case, end-to-end distance L1 is a distance from the end of the crimped fiber to the boundary part at which the fiber is buried inside the non-woven fabric. On the other hand, fiber length L2 is a length of the fiber of the observable part of the crimped fiber (the part from the end of the crimped fiber to the point where it is buried inside the non-woven fabric) extended two-dimensionally on the photograph.

FIG. 1(b) shows a composite fiber in which both ends are buried inside the non-woven fabric, and in this case, end-to-end distance L1 is a distance between both ends in the part exposed on the surface of the non-woven fabric (both ends on the photograph). On the other hand, fiber length L2 is a length of the crimped fiber of the part exposed on the surface of the non-woven fabric extended two-dimensionally on the photograph.

[6] Mass Per Unit Area

Measurement was conducted in conformity with JIS L 1913 "Test methods for nonwovens".

[7] Thickness and Density

Thickness was measured in conformity with JIS L 1913 "Test methods for nonwovens", and density was calculated from this value and the mass per unit area measured in the method of "6.".

[8] Breaking Strength and Breaking Elongation

Breaking strength and breaking elongation were measured in conformity with JIS L 1913 "Test methods for nonwovens". Breaking strength and breaking elongation were measured for the machine direction (MD) and the width (CD) direction of the non-woven fabric.

[9] Recovery Rate after 50% Extension

A tensile test in conformity with JIS L 1913 "Test methods for nonwovens" was conducted, and recovery rate after 50% extension was determined based on the following formula:

Recovery rate after 50% extension (%)=100−X

In the formula, X represents a residual strain (%) when a load is removed immediately after the extension has reached 50% in the tensile test. Recovery rate after 50% extension was measured for the MD direction and the CD direction.

[10] Stress-Strain Curve (S-S Curve)

A stress-strain curve was measured for the MD direction in conformity with JIS L 1913 "Test methods for nonwovens", and stresses $\sigma_{20}$, $\sigma_{30}$, $\sigma_{55}$, $\sigma_{65}$ and $\sigma_{80}$ at a strain $\varepsilon$ (elongation) of 20, 30, 55, 65, and 80% were determined. FIGS. 2 to 6 show stress-strain curves obtained in each of Examples and Comparative Examples. Also based on these stress values, a ratio $(\sigma_{65}-\sigma_{55})/(\sigma_{30}-\sigma_{20})$ of the rates of change in stress was calculated.

[11] Change in Strain by 20 N/50 mm Extension Repetition Test

In the tensile test in conformity with JIS L 1913 "Test methods for nonwovens", a test of repeating an operation of extending in the MD direction so that the stress was 20 N/50 mm and recovering the strain to the original position without a waiting time, successively a total of five times was conducted, and strain $\varepsilon$ (%) after operation of each time of the total of five times was measured. Also, a strain variation was calculated according to the following formula:

Strain variation=strain $\varepsilon$ of the fifth time−strain $\varepsilon$ of the first time Example 1

As a potential crimpable fiber, a side-by-side type composite staple fiber ["PN-780" available from KURARAY CO., LTD., 1.7 dtex×51 mm long, machine crimp number: 12 crimps/25 mm, number of crimps after heating at 130° C. for 1 minute: 62 crimps/25 mm) composed of a polyethylene terephthalate resin having an intrinsic viscosity of 0.65 [component (A)], and modified polyethylene terephthalate resin [component (B)] in which 20 mol % of isophthalic acid and 5 mol % of diethylene glycol are copolymerized, was prepared. Using 100% by mass of this side-by-side type composite staple fiber, a carded web having a mass per unit area 45.5 g/m² was provided by a carding method.

This carded web was moved on the conveyer belt, and allowed to pass between the conveyer belt and a porous plate drum having pores (circular) with a diameter of 2 mmϕ arranged at a pitch of 2 mm in a hound's tooth check, and from inside the porous plate drum, a water flow was injected in a spray form at 0.8 MPa toward the web and the conveyer net, and thus a localizing step for periodically forming a low-density region and a high-density region of fibers was conducted.

Then while the carded web was transferred to the belt conveyer equipped with an endless belt formed of resin having 76 mesh and a width of 500 mm, water was injected from nozzles to make fibers be intermingled by using a nozzle in which orifices with a diameter of 0.1 mm are aligned at an interval of 0.6 mm in the width direction of the web, in two stages for each of the front and the back sides (entangling step). Regarding the water pressure, in the nozzle line of the former stage, spraying was conducted at 2 MPa for both the front and the back sides, and in the nozzle line of the latter stage, spraying was conducted at 4 MPa for both the front and the back sides.

Then the fiber web was transferred to the heating step while the web was overfed at about 150% so as not to interfere with the contraction in the next heating step with the water vapor. In the belt conveyer used herein, an identical belt is provided above the belt of this belt conveyer, and these belts rotate in the same direction at the same speed, and the interval between these belts can be arbitrarily adjusted.

Then, the fiber web was introduced into the water-vapor injecting device provided in the belt conveyer, and water vapor at 0.4 MPa was ejected to the fiber web perpendicularly from the water-vapor injecting device to conduct a water vapor treatment to cause emergence of coiled crimps of the potential crimped fibers, and cause intermingling of fibers, and thus a non-woven fabric was obtained. This water-vapor injecting device was provided in such a manner that a nozzle was installed in one conveyer so as to spray water vapor toward the fiber web via the conveyer belt, and a suction device was installed in the other conveyer. However, the suction was not operated. The pore diameter of the water vapor injecting nozzle was 0.3 mm, and a device in which this nozzle was arranged in one line at a pitch of 2 mm in the width direction of the conveyer was used. The processing speed was 10 m/minute, and the distance between the nozzle and the conveyer belt of the suction side was 10 mm.

The obtained non-woven fabric showed excellent self-adhesiveness, and stretched well both in the MD direction and in the CD direction, and recovered the original shape when the stress was released after being extended lightly with hands to such a degree that the non-woven fabric was not broken. The evaluation result of the obtained non-woven fabric is shown in Table 1.

Observation of the surface and the section in the thickness direction of the obtained non-woven fabric under an electron microscope (100-power) revealed that fibers were oriented substantially parallel with the plane direction of the non-woven fabric, and crimped substantially uniformly in the thickness direction.

Example 2

Using 100 mass % of the same side-by-side type composite staple fiber as used in Example 1, a carded web having a mass per unit area of 78.4 g/m$^2$ was prepared by the carding method. A stretchable non-woven fabric was prepared in the same manner as in Example 1 except that this carded web was used.

The obtained non-woven fabric showed excellent self-adhesiveness, and stretched well both in the MD direction and in the CD direction, and recovered the original shape when the stress was released after being extended lightly with hands to such a degree that the non-woven fabric was not broken. The evaluation result of the obtained non-woven fabric is shown in Table 1.

Observation of the surface and the section in the thickness direction of the obtained non-woven fabric under an electron microscope (100-power) revealed that fibers were oriented substantially parallel with the plane direction of the non-woven fabric, and crimped substantially uniformly in the thickness direction.

Comparative Example 1

Using 100 mass % of the same side-by-side type composite staple fiber as used in Example 1, a carded web having a mass per unit area of 25.7 g/m$^2$ was prepared by the carding method. A stretchable non-woven fabric was prepared in the same manner as in Example 1 except that this carded web was used, and the entangling step was not conducted after execution of the localizing step.

The obtained non-woven fabric had stretchability and self-adhesiveness, but was poor in breaking strength. In the 20 N/50 mm extension repetition test, breakage occurred in the non-woven fabric sample, so that strain ε and strain variation could not be measured. Observation of the surface and the section in the thickness direction of the obtained non-woven fabric under an electron microscope (100-power) revealed that fibers were oriented substantially parallel with the plane direction of the non-woven fabric, and crimped substantially uniformly in the thickness direction.

Comparative Example 2

Using 100 mass % of the same side-by-side type composite staple fiber as used in Example 1, a carded web having a mass per unit area of 37.8 g/m$^2$ was prepared by the carding method. A stretchable non-woven fabric was prepared in the same manner as in Example 1 except that this carded web was used, and the entangling step was not conducted after execution of the localizing step.

The obtained non-woven fabric had stretchability and self-adhesiveness, but had low breaking strength and repetition durability, and was susceptible to deterioration in stretchability by repeated use. Observation of the surface and the section in the thickness direction of the obtained non-woven fabric under an electron microscope (100-power) revealed that fibers were oriented substantially parallel with the plane direction of the non-woven fabric, and crimped substantially uniformly in the thickness direction.

Comparative Example 3

As a wet heat adhesive fiber, a core-clad type composite staple fiber ["S220" available from KURARAY CO., LTD., 3.3 dtex×51 mm long, core-clad mass ratio=50/50, machine crimp number: 21 crimps/25 mm] composed of polyethylene terephthalate as a core component, and an ethylene-vinyl alcohol copolymer (ethylene content: 44 mol %, degree of saponification: 98.4 mol %) as a clad component was prepared. Using 30 mass % of this core-clad type composite staple fiber, and 70 mass % of the same side-by-side type composite staple fiber as used in Example 1, a carded web having a mass per unit area of 65.8 g/m$^2$ was prepared by the carding method. A stretchable non-woven fabric was prepared in the same manner as in Example 1 except that this carded web was used, and the entangling step was not conducted after execution of the localizing step.

The obtained non-woven fabric had stretchability and self-adhesiveness, but had low breaking strength and repetition durability, and was susceptible to deterioration in stretchability by repeated use. Observation of the surface and the section in the thickness direction of the obtained non-woven fabric under an electron microscope (100-power) revealed that fibers were oriented substantially parallel with the plane direction of the non-woven fabric, and crimped substantially uniformly in the thickness direction.

TABLE 1

|  |  | Example 1 | Example 2 | Comparative Example 1 | Comparative Example 2 | Comparative Example 3 |
| --- | --- | --- | --- | --- | --- | --- |
| Mean number of coiled crimps | crimps/mm | 8.3 | 7.3 | 8.1 | 8.5 | 5.7 |
| Mean crimping pitch | (μm) | 120 | 137 | 123 | 118 | 176 |
| Mean radius of curvature | (μm) | 62 | 56 | 63 | 62 | 87 |
| Curvature of fiber | Front layer | 1.70 | 1.72 | 1.75 | 1.73 | 1.43 |
|  | Internal layer | 1.63 | 1.58 | 1.43 | 1.54 | 1.23 |
|  | Back layer | 1.72 | 1.61 | 1.67 | 1.67 | 1.48 |
|  | Uniformity (%) | 94.8 | 91.9 | 81.7 | 89.0 | 86.0 |
| Mass per unit area | (g/m$^2$) | 154.2 | 96.2 | 93.6 | 130.0 | 125.1 |
| Thickness | (mm) | 1.7 | 0.9 | 1.3 | 1.0 | 3.0 |
| Density | (g/m$^3$) | 0.09 | 0.11 | 0.07 | 0.13 | 0.04 |

TABLE 1-continued

|  |  | Example 1 | Example 2 | Comparative Example 1 | Comparative Example 2 | Comparative Example 3 |
|---|---|---|---|---|---|---|
| Breaking strength | MD (N/50 mm) | 48.9 | 155.4 | 13.5 | 22.9 | 30.4 |
|  | CD (N/50 mm) | 7.7 | 41.3 | 2.7 | 6.1 | 8.5 |
| Breaking elongation | MD (%) | 91.0 | 147.9 | 100.3 | 120.0 | 101.8 |
|  | CD (%) | 152.9 | 276.6 | 112.8 | 93.2 | 82.6 |
| Recovery rate after 50% extension | MD (%) | 93.6 | 88.8 | 93.9 | 96.4 | 88.2 |
|  | CD (%) | 91.4 | 90.8 | 90.0 | 88.6 | 85.4 |
| Stress-strain curve (MD) | Stress $\sigma_{20}$ (N/50 mm) | 3.5 | 3.4 | 1.3 | 3.8 | 3.5 |
|  | Stress $\sigma_{30}$ (N/50 mm) | 6.7 | 6.0 | 2.3 | 6.3 | 6.1 |
|  | Stress $\sigma_{55}$ (N/50 mm) | 28.4 | 17.1 | 5.0 | 12.2 | 17.2 |
|  | Stress $\sigma_{65}$ (N/50 mm) | 38.1 | 28.4 | 6.3 | 14.7 | 22.3 |
|  | Stress $\sigma_{80}$ (N/50 mm) | 45.9 | 48.6 | 8.5 | 19.2 | 29.1 |
|  | $(\sigma_{65}-\sigma_{55})/(\sigma_{30}-\sigma_{20})$ | 3.1 | 4.4 | 1.4 | 1.0 | 2.0 |
| 20 N/50 mm extension repetition test | Strain $\varepsilon$ (%) First time | 47.0 | 59.0 | Unmeasurable (sheet broken) | 71.0 | 44.9 |
|  | Second time | 47.7 | 59.7 |  | 75.8 | 49.7 |
|  | Third time | 48.2 | 60.2 |  | 78.8 | 53.3 |
|  | Fourth time | 48.6 | 60.4 |  | 81.2 | 56.5 |
|  | Fifth time | 48.9 | 60.6 |  | 83.0 | 59.3 |
|  | Strain variation | 1.9 | 1.6 |  | 12.0 | 14.4 |

The invention claimed is:

1. A stretchable non-woven fabric comprising crimped fibers, satisfying the following formula:

$$(\sigma_{65}-\sigma_{55})/(\sigma_{30}-\sigma_{20}) \geq 3.5$$

wherein $\sigma_{20}$, $\sigma_{30}$, $\sigma_{55}$ and $\sigma_{65}$ area stress $\sigma$ (N/50 mm) at a strain $\varepsilon$ of 20%, 30%, 55%, and 65% in a stress-strain curve by a tensile test for a machine direction (MD) in a manufacturing process or a longitudinal direction in a sheet plane, respectively, wherein the stretchable non-woven fabric is produced by the following method comprising:

webbing fibers comprising a composite fiber, thereby making a composite fiber web, making the fibers in the composite fiber web localized in a plane prior to entangling the fibers by spraying or injecting low-pressure water intermittently or periodically to the composite fiber web to form a plurality of low-density parts and a plurality of high-density parts alternately and periodically, entangling the fibers in the composite fiber web by spraying or injecting water, and heating the composite fiber web to crimp the composite fiber, wherein breaking strength of the stretchable non-woven fabric by a tensile test for the machine direction (MD) or the longitudinal direction in the sheet plane and in a direction (a CD direction) orthogonal to the machine direction (MD) or in a width direction in the sheet plane is at least 40 N/50 mm, wherein a stress σ80 at a strain $\varepsilon$ of 80% is greater than or equal to at least 20 N/50 mm, wherein a jet pressure of the water for entangling the fibers in the fiber web is greater than a jet pressure of the water for making the fibers in the composite fiber web localized in a plane, and wherein the stretchable non-woven fabric has a mass per unit area of from 90 g/m² to 96.2 g/m².

2. The stretchable non-woven fabric according to claim 1, wherein the crimped fibers are formed of a composite fiber in which a plurality of resins having different coefficients of thermal contraction form a phase structure and are oriented substantially parallel with a plane direction, and are crimped substantially uniformly in a thickness direction, and wherein the crimped fibers have a mean radius of curvature of from 20 to 200 μm.

3. The stretchable non-woven fabric according to claim 1 that is a bandage.

4. The stretchable non-woven fabric according to claim 1, wherein $$(\sigma_{65}-\sigma_{55})/(\sigma_{30}-\sigma_{20}) \geq 4.0.$$

5. The stretchable non-woven fabric according to claim 1, wherein the breaking strength by a tensile test for the machine direction (MD) or the longitudinal direction in the sheet plane is at least 60 N/50 mm.

6. The stretchable non-woven fabric according to claim 1, wherein the breaking strength by a tensile test for the machine direction (MD) or the longitudinal direction in the sheet plane is not more than 200 N/50 mm.

7. The stretchable non-woven fabric according to claim 1, wherein the breaking strength by a tensile test for the machine direction (MD) or the longitudinal direction in the sheet plane is not more than 180 N/50 mm.

8. The stretchable non-woven fabric according to claim 1, wherein breaking elongation for the machine direction (MD) or the longitudinal direction in the sheet plane is at least 90%.

9. The stretchable non-woven fabric according to claim 1, wherein a recovery rate after 50% extension for the machine direction (MD) or the longitudinal direction in the sheet plane is at least 70%.

10. The stretchable non-woven fabric according to claim 1, wherein a mass per unit area is from 95 g/m² to 96.2 g/m².

11. The stretchable non-woven fabric according to claim 1, wherein a bulk density of the stretchable non-woven fabric is from 0.01 to 0.5 g/cm³.

12. The stretchable non-woven fabric according to claim 1, wherein air permeability of the stretchable non-woven fabric is from 1 to 500 cm³/cm²·sec.

13. The stretchable non-woven fabric according to claim 1, wherein the composite fiber has a hollow section in a cross section.

14. The stretchable non-woven fabric according to claim 1, wherein a core is formed from a resin having a melting point or softening point different from a resin of a clad, wherein the clad surrounds the core, and wherein thermal contractions of the clad and the core are different.

15. The stretchable non-woven fabric according to claim 1, wherein a mean fiber length of the composite fiber is from 10 to 100 mm.

\* \* \* \* \*